United States Patent
Lichtenstein et al.

(10) Patent No.: US 10,588,809 B2
(45) Date of Patent: Mar. 17, 2020

(54) CABLE ARRANGER

(71) Applicant: BIOSENSE WEBSTER (ISRAEL) LTD., Yokneam (IL)

(72) Inventors: Yoav Lichtenstein, Raanana (IL); Dudu Haimovich, Ramat Yishai (IL); Roee Haimovich, Nesher (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1174 days.

(21) Appl. No.: 14/147,831

(22) Filed: Jan. 6, 2014

(65) Prior Publication Data

US 2015/0190610 A1    Jul. 9, 2015

(51) Int. Cl.
| | | |
|---|---|---|
| *A61M 25/01* | (2006.01) | |
| *A61G 13/10* | (2006.01) | |
| *A61B 34/20* | (2016.01) | |
| *A61B 90/00* | (2016.01) | |

(52) U.S. Cl.
CPC ....... *A61G 13/101* (2013.01); *A61M 25/0133* (2013.01); *A61B 2034/2048* (2016.02); *A61B 2034/2051* (2016.02); *A61B 2090/031* (2016.02); *A61B 2090/066* (2016.02); *A61B 2090/067* (2016.02); *A61G 2203/20* (2013.01); *A61G 2203/42* (2013.01)

(58) Field of Classification Search
CPC ........ A61M 25/0113; A61M 25/09041; A61M 2205/103; A61B 2034/301; A61B 1/0016; A61B 2018/00208; A61G 13/101
See application file for complete search history.

(56) References Cited

U.S. PATENT DOCUMENTS

| | | | |
|---|---|---|---|
| 4,061,381 A | | 12/1977 | Smal |
| 5,338,314 A | * | 8/1994 | Ryan ................ A61M 39/0613 604/167.06 |
| 5,352,197 A | | 10/1994 | Hammersmark et al. |
| 5,921,978 A | | 7/1999 | Thompson et al. |
| 6,309,370 B1 | * | 10/2001 | Haim ................ A61M 25/0075 604/66 |
| 2005/0272976 A1 | * | 12/2005 | Tanaka ............... A61B 1/00073 600/114 |

(Continued)

FOREIGN PATENT DOCUMENTS

| | | |
|---|---|---|
| CN | 101773699 A | 7/2010 |
| CN | 102227079 A | 10/2011 |

(Continued)

OTHER PUBLICATIONS

EP Examination Report for EP15150090.7 dated Mar. 16, 2016.

(Continued)

*Primary Examiner* — Bhisma Mehta
*Assistant Examiner* — Hamza A Darb
(74) *Attorney, Agent, or Firm* — Louis J. Capezzuto (57) ABSTRACT

Catheterization employing a cable extending from the catheter to a fixed point of attachment is performed by providing a sensor to detect rotation of the catheter about its longitudinal axis, the rotation causing the cable to form a twist. The cable extends through a cable arranger that operates to remove the twist. A controller receives signals from the sensor and generates control signals to actuate the cable arranger responsively to the signals from the sensor.

10 Claims, 10 Drawing Sheets

(56) References Cited

U.S. PATENT DOCUMENTS

| | | | |
|---|---|---|---|
| 2006/0058667 A1 | 3/2006 | Lemmerhirt et al. | |
| 2006/0229587 A1* | 10/2006 | Beyar | A61M 25/0113 |
| | | | 604/510 |
| 2008/0051727 A1* | 2/2008 | Moberg | A61M 5/14248 |
| | | | 604/207 |
| 2010/0137837 A1 | 6/2010 | Govari | |
| 2011/0137151 A1 | 6/2011 | Lichtenstein | |
| 2012/0035467 A1* | 2/2012 | Lichtenstein | A61B 5/062 |
| | | | 600/424 |
| 2013/0023770 A1 | 1/2013 | Courtney | |
| 2015/0173829 A1* | 6/2015 | Lichtenstein | A61B 18/1492 |
| | | | 606/34 |

FOREIGN PATENT DOCUMENTS

| | | |
|---|---|---|
| EP | 2415399 A1 | 2/2012 |
| EP | 2893896 A1 | 7/2015 |
| JP | S48-33179 | 7/1971 |
| JP | H11-99493 | 4/1999 |
| JP | 2012-35080 | 2/2012 |

OTHER PUBLICATIONS

European Search Report dated Jun. 15, 2015 for corresponding Application No. EP15150090.
U.S. Appl. No. 14/139,974, filed Dec. 24, 2013.
Chinese Office Action dated Sep. 18, 2018—English translation.
JPH11099493—Derwent English translation of Abstract.
EPO Patent Machine translation description.
Abstract Translation for CN102227079A.
CN Translation of Office Action dated Dec. 4, 2018.

\* cited by examiner

CABLE ARRANGER

BACKGROUND OF THE INVENTION

Field of the Invention

This invention relates to medical devices. More particularly, this invention relates to placement and operation of probes within the body of a subject.

Description of the Related Art

When a physician manipulates a catheter during a medical procedure, the catheter may become twisted or tangled. Several methods and systems have been proposed in order to detect or avoid such situations. For example, U.S. Pat. No. 5,921,978, whose disclosure is incorporated herein by reference, describes a catheter that includes fluoroscopic marker components. Some of the disclosed catheter configurations are used for providing visual information to the physician regarding the direction and degree of twist of the catheter distal end.

U.S. Pat. No. 5,352,197, whose disclosure is incorporated herein by reference, describes a turn limiter for a catheter with a twistable tip. The catheter has a flexible wall for use in complex twisting anatomy, and contains a torque wire or a torquable guide wire lumen. The torque wire or torquable guide wire lumen extends through the length of the catheter and is attached to the catheter at or near the distal end thereof. The proximal end of the torque wire protrudes from the proximal end of the catheter and is attached to a turn limiter. The turn limiter allows limited rotation of the proximal end of the torque wire or torquable guide wire lumen without axial dislocation.

U.S. Patent Application Publication No. 2012/0035467, commonly assigned herewith and herein incorporated by reference, describes a catheter entanglement limiter. An operator of an elongated probe manipulates the proximal end of the probe so as to move the distal end within a body of a patient, automatically measuring a cumulative angle of rotation that is applied by the operator to the proximal end. An indication of the cumulative angle of rotation is presented to the operator.

SUMMARY OF THE INVENTION

There is provided according to embodiments of the invention a catheter adapted for insertion into a living subject, the catheter having a longitudinal axis, a cable having one end attached to the catheter and another end to a fixed point, a sensor for detecting rotation of the catheter about the longitudinal axis, the rotation causing a portion of the cable to form a twist, a cable arranger for removing the twist from the portion of the cable, and a controller receiving signals from the sensor and operative for generating control signals to actuate the cable arranger responsively to the signals of the sensor.

According to an aspect of the apparatus, the sensor is a magnetic field sensor.

According to another aspect of the apparatus, the sensor is an accelerometer adapted to measure tangential acceleration of the catheter about the longitudinal axis.

According to another aspect of the apparatus, the sensor is a rotary torque transducer.

According to one aspect of the apparatus, the cable arranger includes a shaft holding a segment of the cable, and a drive motor for rotating the shaft.

According to a further aspect of the apparatus, the shaft has a lumen, the cable passing through the lumen and is in contact with the shaft for rotation therewith.

An additional aspect of the apparatus includes a gear train linked to the drive motor and the shaft.

According to another aspect of the apparatus, the gear train includes a drive gear attached to the drive motor, two linking gears meshing with the drive gear, and a shaft gear meshing with the two linking gears. The shaft gear is concentric with the shaft and has a radial slot for insertion and removal of the cable therethrough. The cable is wound about the shaft.

According to still another aspect of the apparatus, spiral grooves are formed in the shaft for carrying the cable therein.

One aspect of the apparatus includes a drive gear attached to the drive motor that meshes with gear teeth formed on the shaft. The cable is urged into contact with grooves in the drive gear when the spiral grooves and the grooves of the drive gear are in alignment.

There is further provided according to embodiments of the invention a method, which is carried out by inserting a catheter into a living subject, connecting a cable between the catheter and a fixed point of attachment, forming a twist in a portion of the cable by rotating the catheter about its longitudinal axis, automatically detecting rotation of the catheter about the longitudinal axis, and responsively to detecting rotation removing the twist from the portion of the cable.

According to a further aspect of the method, detecting rotation is performed using a magnetic field sensor.

According to one aspect of the method, detecting rotation is performed using an accelerometer adapted to measure tangential acceleration of the catheter about the longitudinal axis.

According to another aspect of the method, detecting rotation is performed using a torque transducer.

According to an additional aspect of the method, removing the twist is performed by operating a cable arranger including a shaft holding a segment of the cable, and a drive motor for rotating the shaft, and imparting a compensatory rotation about the longitudinal axis of the cable.

Yet another aspect of the method includes providing a cable arranger having a drive gear, the drive gear having grooves formed therein. The drive gear is attached to a drive motor and a shaft having spiral grooves formed therein for carrying the cable, the drive gear meshing with gear teeth formed on the shaft, wherein the cable is urged into contact with the grooves of the drive gear when the spiral grooves of the shaft and the grooves of the drive gear are in alignment, wherein removing the twist comprises rotating the shaft to displace the cable through the cable arranger.

A further aspect of the method includes providing a radial slot in the drive gear for ingress and egress of the cable therethrough.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention.

Figure 1:
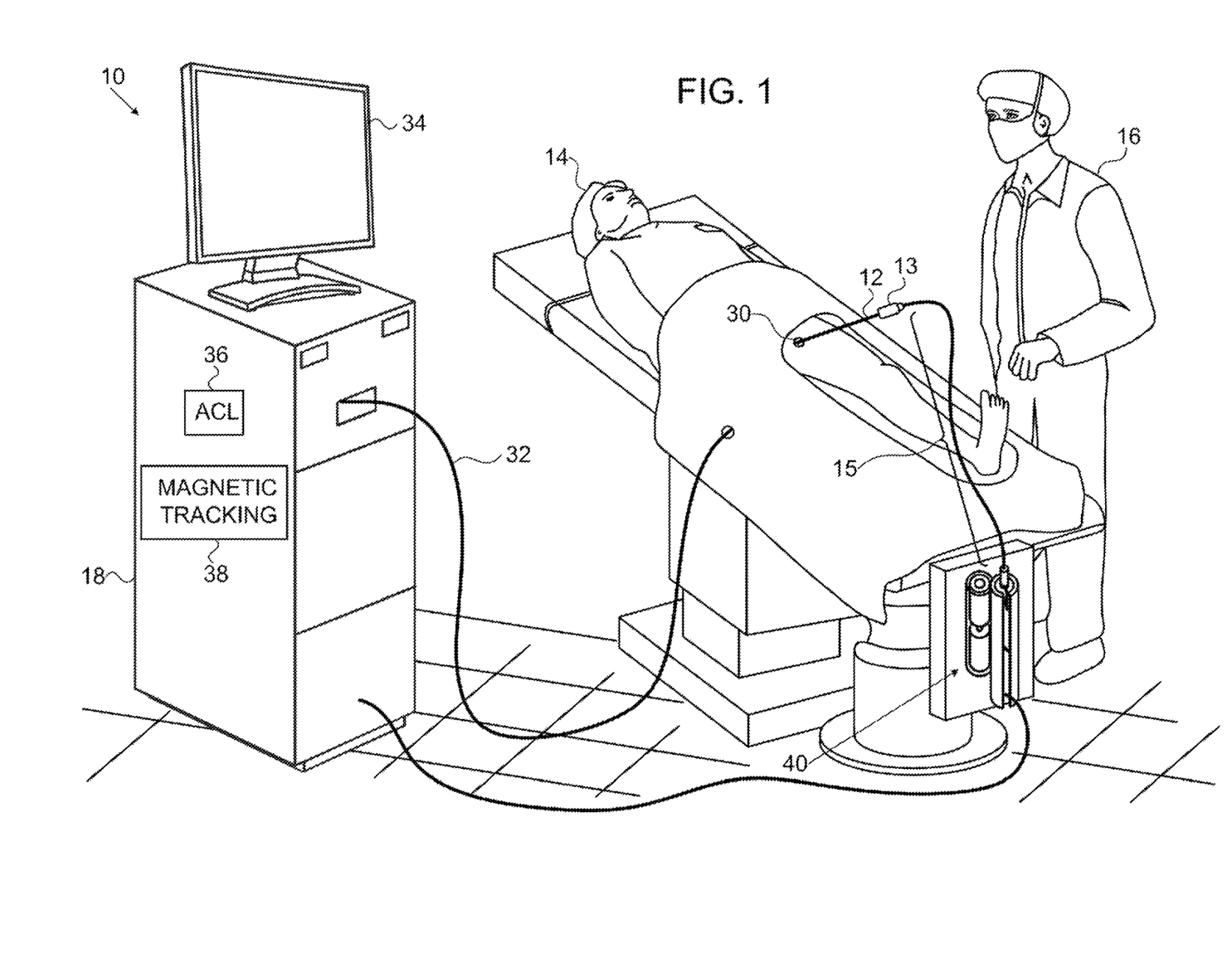
FIG. 1 is a schematic illustration of a cable arranger for use with a position tracking system, in accordance with an embodiment of the present invention.

Turning now to the drawings, Reference is initially made to FIG. 1, which is a schematic, pictorial illustration of a position tracking system 10, in accordance with an embodiment of the present invention. Typically, a catheter 12 that can be navigated with a handle 13 is used for diagnostic or therapeutic treatment performed by medical practitioner 16, such as mapping electrical potentials in the heart or performing ablation of heart tissue. The catheter 12 or other intrabody device may alternatively be used for other purposes, by itself or in conjunction with other treatment devices. The catheter 12 enters a subject 14 at an insertion point 30, which in this example is a femoral vessel. Processors and circuitry related to the medical procedure are found in a control unit 18. The system 10 typically includes a subsystem for tracking the position of the catheter 12 within the body of the subject 14. One tracking sub-system of the system 10 is known as an active current localization ACL subsystem 36, in which a plurality of body-surface electrodes are placed in galvanic contact with a body-surface, e.g., the skin of the subject 14, and receive body surface currents therefrom. Additionally or alternatively, the system 10 may include a magnetic tracking sub-system 38 comprising magnetic sensors and field generators for tracking the catheter 12. Processors for the subsystems 36, 38 are typically located in the control unit 18. Peripheral elements of the position tracking sub-systems 36, 38 are generally connected to the control unit 18 by a cable 32. Operational information relating to the catheter 12 and the system 10 may be displayed on a monitor 34. One system that embodies the above-described features of the system 10 is the CARTO® 3 System, available from Biosense Webster, Inc., 3333 Diamond Canyon Road, Diamond Bar, Calif. 91765. This system may be modified by those skilled in the art to embody the principles of the invention described herein.

A cable arranger 40 is operative to prevent undesired twisting and entanglement of a segment 15 of cable near the handle 13 of the catheter 12, where the twisted cable would interfere with the practitioner 16, The cable passes from the catheter 12 through the cable arranger 40 to a fixed point of attachment, such as the control unit 18. The cable may include or be accompanied by one or more hydraulic lines.

Figure 2:
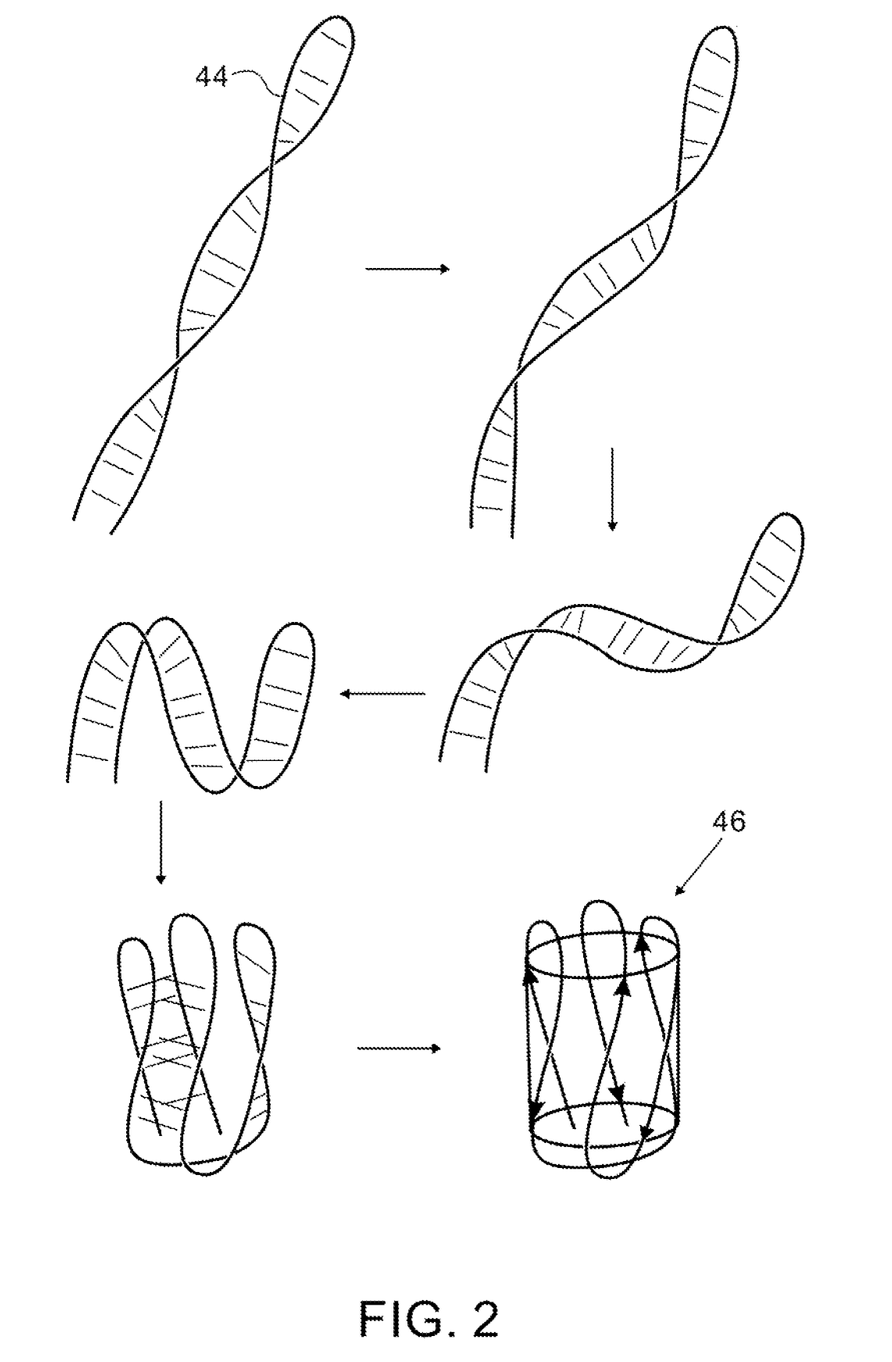
FIG. 2 is a series of images showing a progression of twists of a cable that are compensated using the embodiment of FIG. 1, in accordance with an embodiment of the invention.

Reference is now made to FIG. 2, which is a series of images showing a progression of twists of a cable 44 having one end attached to a catheter and another end attached to a fixed point, e.g., the control unit 18 (FIG. 1). Such twisting can be caused by rotation of the catheter about its longitudinal axis during a catheterization session in the absence of the cable arranger 40. In a worst case 46, the cable 44 becomes a severe encumbrance and can greatly hinder the practitioner 16 in performing the medical procedure.

Figure 3:
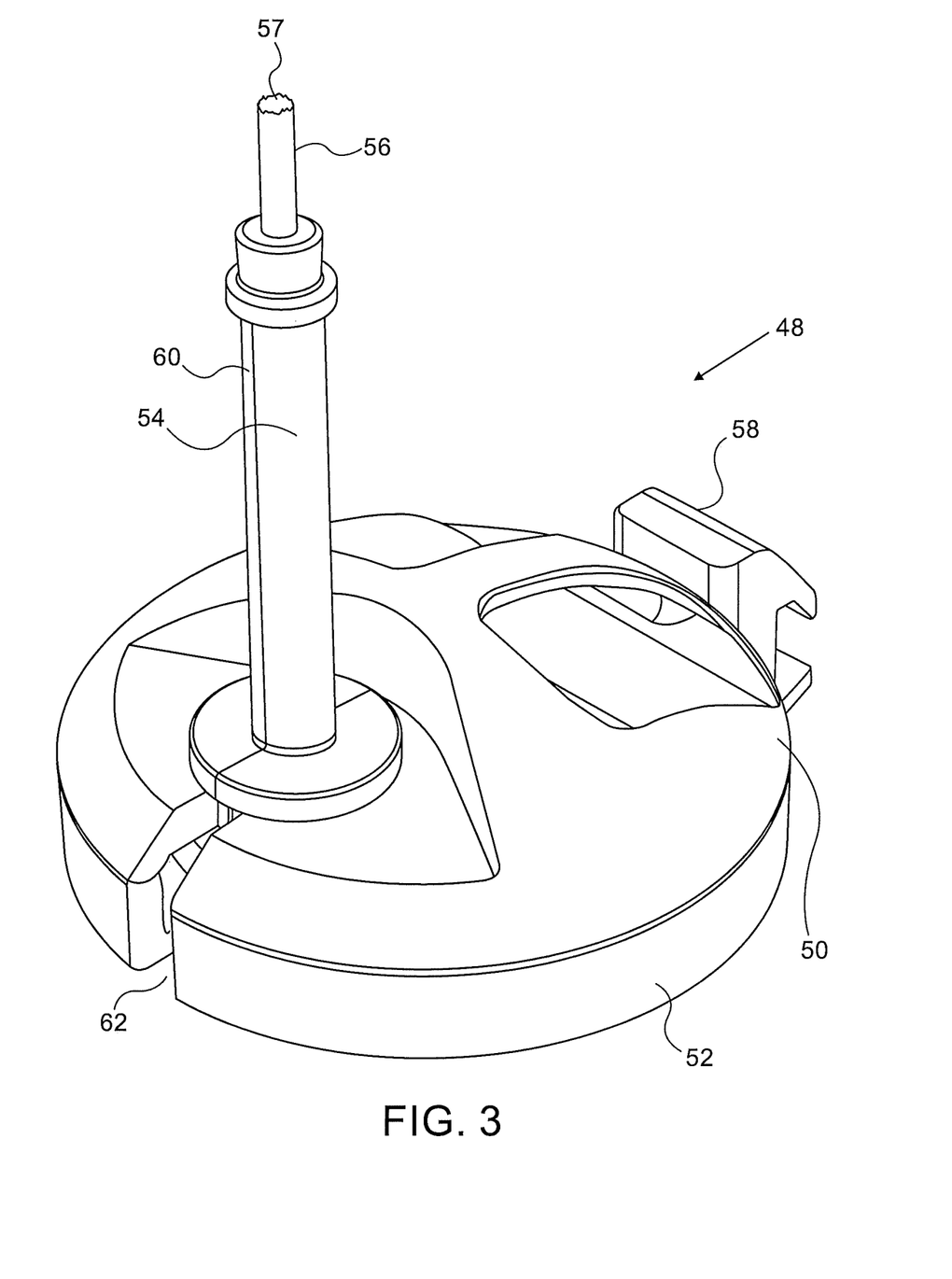
FIG. 3 is a perspective top view of a cable arranger in accordance with an embodiment of the invention.

Reference is now made to FIG. 3, which is a perspective top view of a cable arranger 48, which is a variant of the cable arranger 40 (FIG. 1) in accordance with an embodiment of the invention. A cover 50 and a base 52 comprise a housing for a drive assembly (not shown in this view). A torsion rod 54 extends outward from the cover 50 and grips a cable 56 passing through the torsion rod 54. A clamp 58 is provided for affixing the cable arranger 48 to a convenient attachment point to assure mechanical stability. One or more hydraulic lines 57, e.g., irrigation tubes may be included in the cable 56 or accompany the cable 56 as separate channels to form a bundle of electrical and hydraulic channels 57.

The torsion rod 54 comprises two portions joined together at a seam 60. The two portions can be readily snapped together, allowing the operator to accordingly engage and disengage the cable 56 sideways through a slot 62 formed in the base 52.

Figure 4:
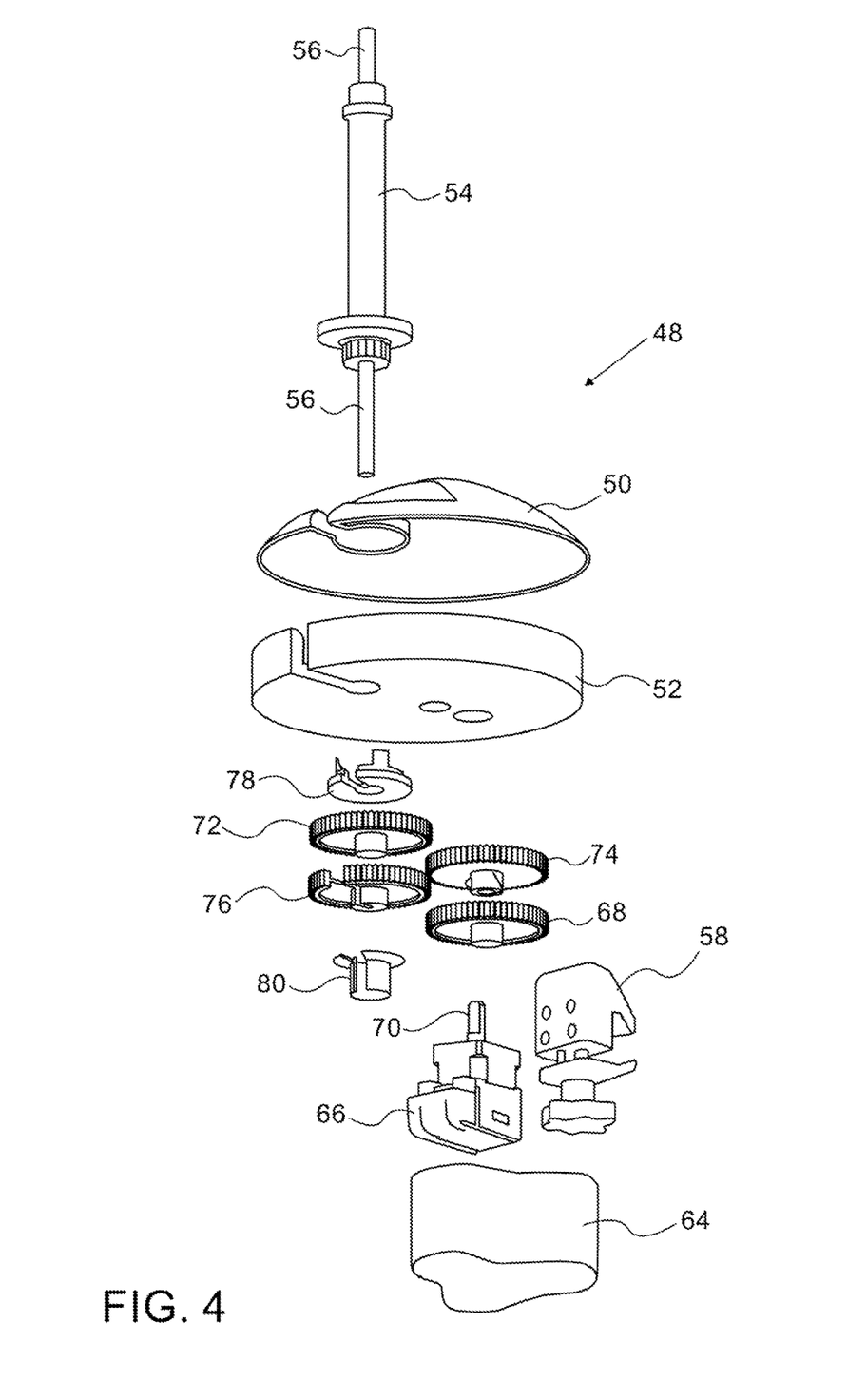
FIG. 4 is an exploded view in slight perspective of the cable arranger shown in FIG. 3, in accordance with an embodiment of the invention.

Reference is now made to FIG. 4, which is an exploded view in slight perspective of the cable arranger 48 (FIG. 3). Mounted beneath the base 52 are a motor cover 64, motor 66 and gear train for rotating the torsion rod 54. The gear train is a modified planetary arrangement comprising a drive gear 68 that is rotated by a drive shaft 70 of the motor 66.

Figure 5:
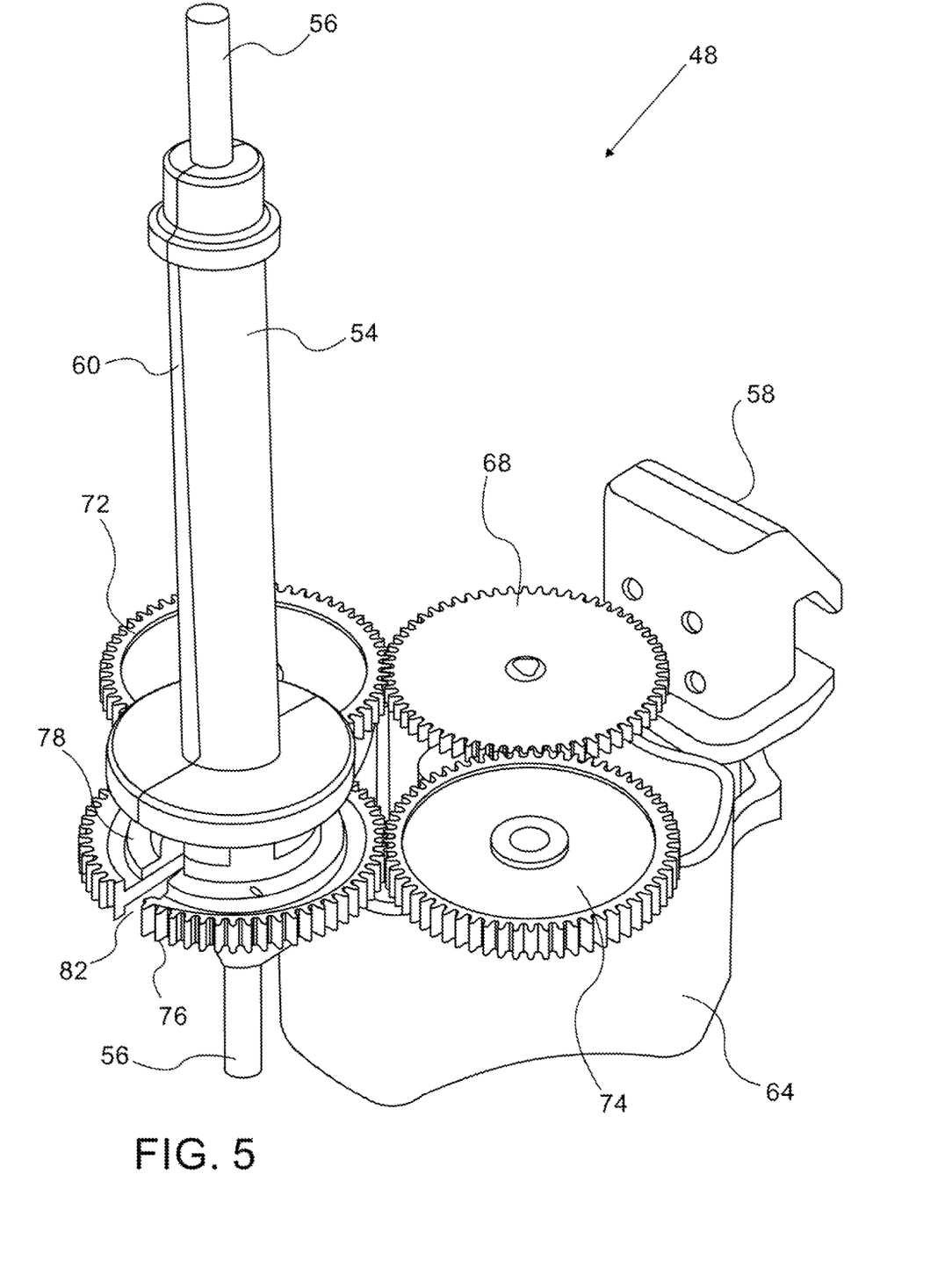
FIG. 5 is a perspective view of the cable arranger shown in FIG. 3 with the housing removed, in accordance with an embodiment of the invention.

Reference is now made to FIG. 5, which is a perspective view of the cable arranger 48 with the housing removed. The gear train is best appreciated in FIG. 5. The drive gear 68 meshes with linking gears 72, 74, both of which mesh with a gear 76 that rotates the torsion rod 54 about its longitudinal axis.

The gear 76 is provided with a slot 82, which provides lateral egress and ingress to the cable 56 when the slot 82 is aligned with the slot 62 (FIG. 3). When the gear 76 is rotated such that the slot 82 opposes one of the gears 72, 74 and is thus unable to mesh with its teeth, the other of the gears 72, 74 continues to mesh and enables further rotation of the gear 76 in either direction.

Figure 6:
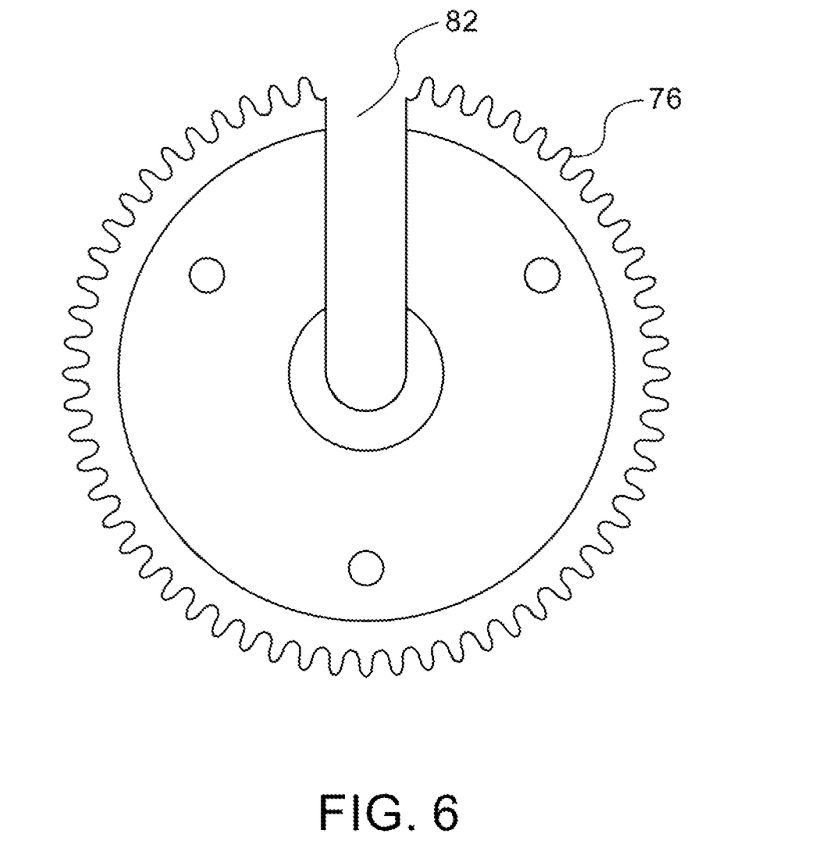
FIG. 6 is an elevation of a gear shown in FIG. 4, in accordance with an embodiment of the invention.

Reference is now made to FIG. 6, which is an elevation of the gear 76. The slot 82 extends radially from the center outward and interrupts the gear teeth. The slot 82 accommodates the cable 56 (FIG. 5).

First Alternate Embodiment

Figure 7:
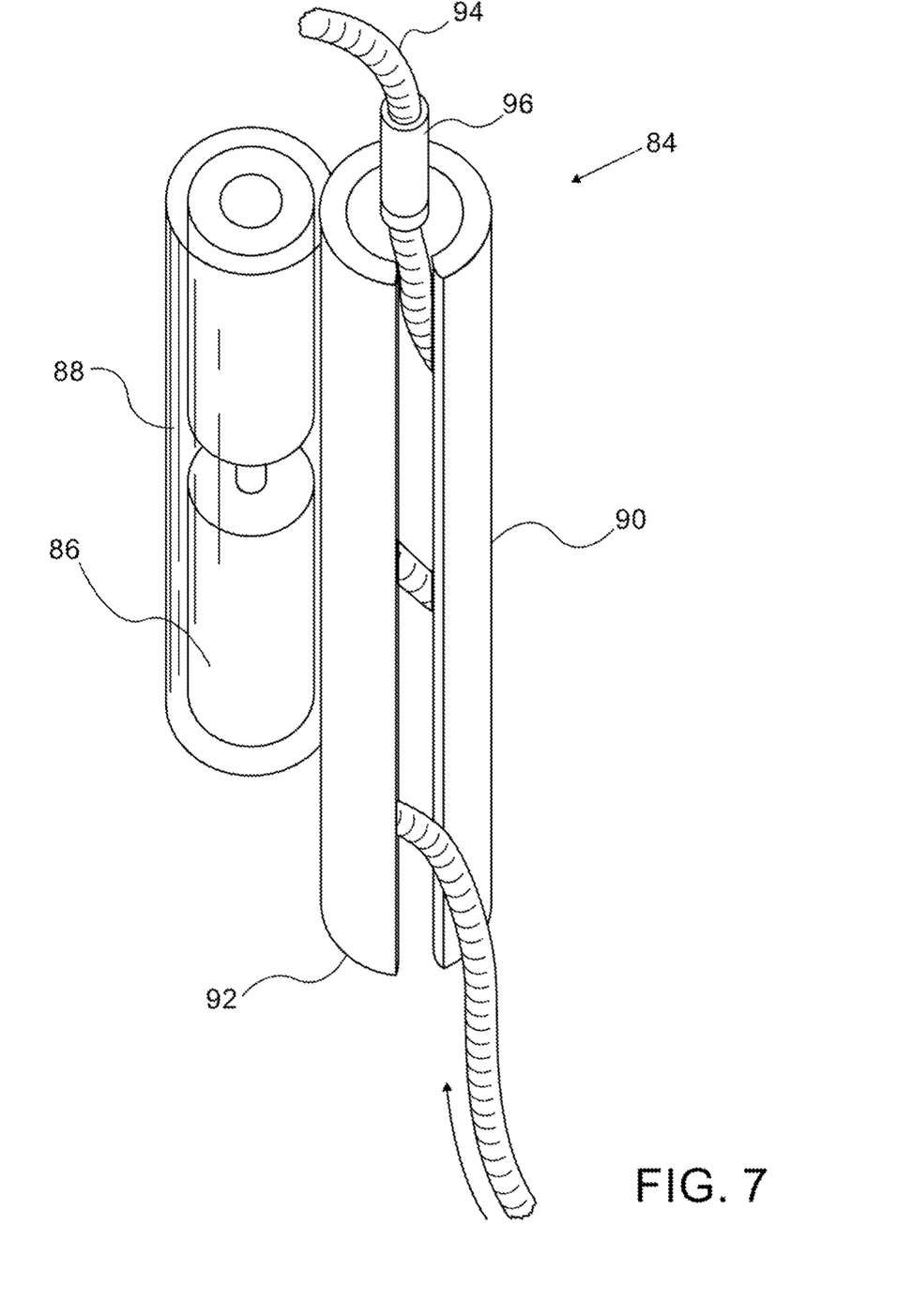
FIG. 7 is a schematic diagram of a cable arranger, in accordance with an alternate embodiment of the invention.

Reference is now made to FIG. 7, which is a schematic diagram of a cable arranger 84, in accordance with an alternate embodiment of the invention. In this embodiment, a drive motor 86 within a housing 88 is geared to a cable collector 90, such that actuation of the drive motor 86 causes a shaft in the cable collector 90 to rotate about its longitudinal axis within its housing 92.

A cable 94 passes into the housing 92 via a sleeve adaptor 96, which is fitted loosely about the cable 94 and can rotate about the cable 94 and not grip the cable 94 when the drive motor 86 is actuated. Referring again to FIG. 1, in normal operation the cable 94 extends from the catheter 12 through the cable arranger 84 to the control unit 18. The cable 94 can be inserted or removed through the housing via a slot 97.

Figure 8:
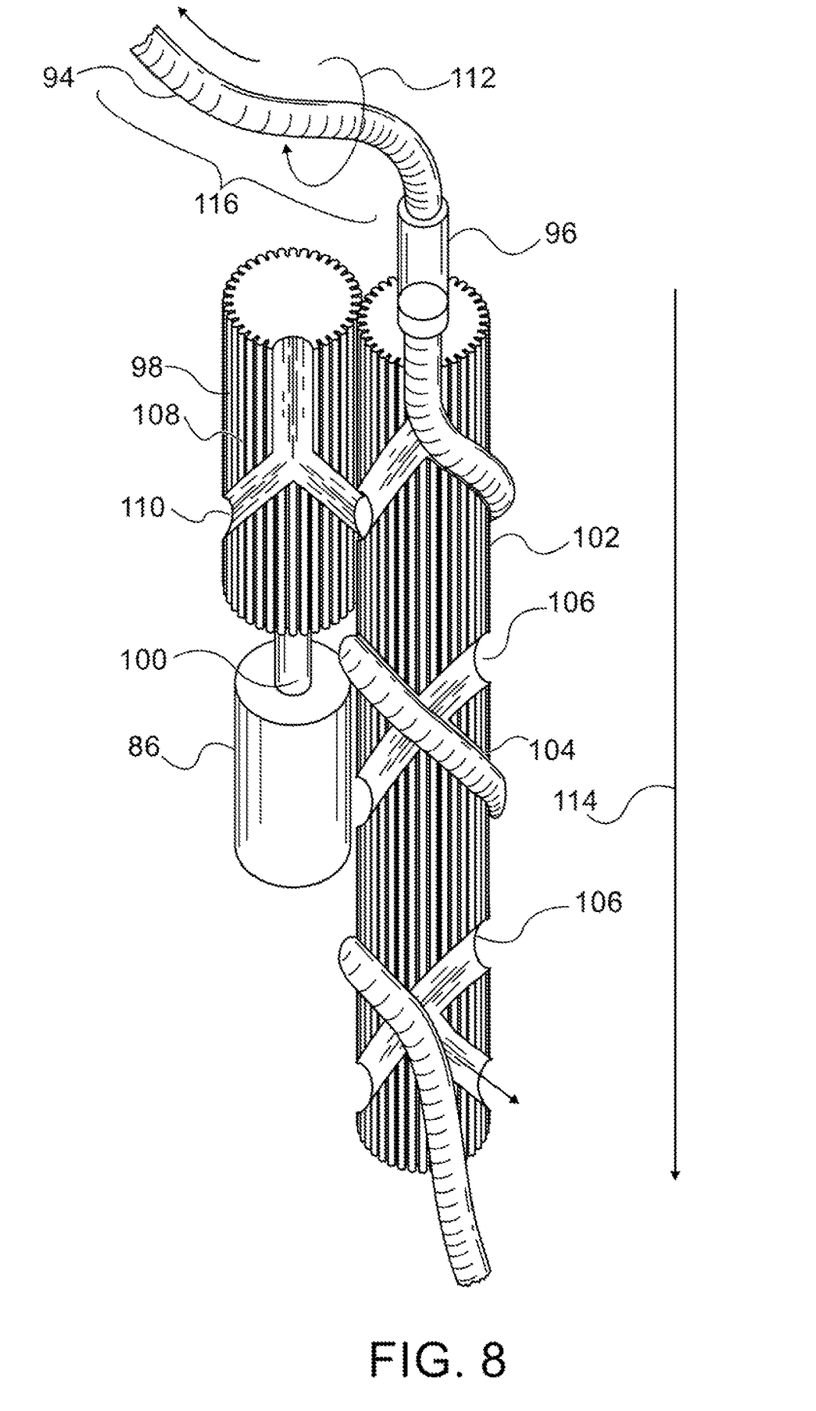
FIG. 8 is a schematic diagram of the cable arranger shown in FIG. 7 with the housings removed.

Reference is now made to FIG. 8, which is a schematic diagram of the cable arranger 84 (FIG. f7|) with the housings removed. The drive motor 86 is connected to a cylindrical drive gear 98 by a drive shaft 100. The drive gear 98 meshes with gear teeth formed on the surface of a cable collector 102, causing the drive gear 98 to contrarotate about its longitudinal axis. Two series of helical grooves 104, 106 are formed in the cable collector 102, one series of grooves having a right-handed and the other a left-handed winding direction. The grooves 104 align with grooves 108 in the drive gear 98. The cable 94 is taken up in the grooves 104, and fits into opposing series of grooves 108 as the drive gear 98 rotates and the grooves 104 align with the grooves 108. The grooves 108 permit take-up of the cable 94 without its being compressed between the drive gear 98 and cable collector 102. Manipulations of the cable 94 by the operator may cause a left-handed or a right-handed twist to form in a segment 116 of the cable 94, and the cable collector 102 rotates in one direction or the other as the case may be so as to compensate. When it is necessary to rotate the cable collector 102 in the opposite direction from that shown in FIG. 8, the cable 94 is carried in the grooves 106 rather than the grooves 104. The grooves 106 align with corresponding grooves 110 in the drive gear 98 and perform the same function as the grooves 108.

When the drive motor 86 is actuated, rotation of the cable collector 102 rotates the cable 94 within the sleeve adaptor 96 in a direction that tends to counteract twisting motion that it may have been subjected to by rotatory movement of the catheter 12 (FIG. 1) as indicated by an arrow 112. However, the principal effect produced by the cable collector 102 is displacement of the twist away from the operator (as indicated by arrow 114), such that the twisted portion of the cable 94 does not occur near the operator (in segment 116), but instead appears beyond the cable collector 102 in segment 118, far enough removed from the operator so as not encumber him during the medical procedure.

Control

Figure 9:
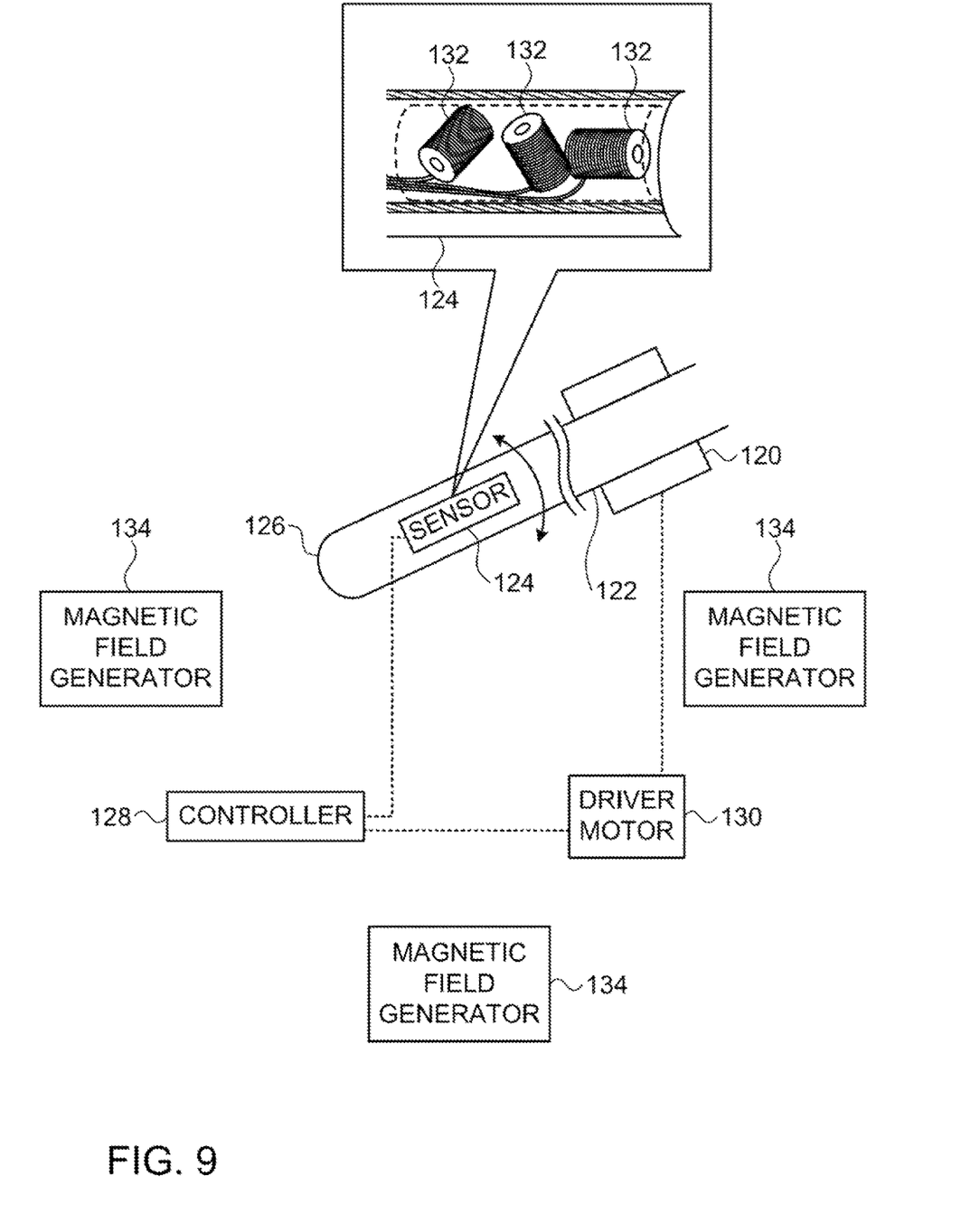
FIG. 9 is a schematic diagram of a control arrangement for a cable arranger, which is constructed and operative in accordance with an embodiment of the invention.

Reference is now made to FIG. 9, which is a schematic diagram of a control arrangement for a cable arranger, which is constructed and operative in accordance with any of the embodiments of the invention described herein. A cable arranger 120, typically located on a portion of a cable 122 proximal to the operator (not shown), acts in response to rotation of the catheter about its longitudinal axis. Rotation is sensed by a sensor 124, which can be disposed on the shaft of the catheter 122 or near its tip 126, or in the handle (not shown) of the catheter.

When a reading of the sensor 124 by a controller 128 indicates that rotation of the catheter is occurring distal to the cable arranger 120 thereby inducing the cable to twist, a drive motor 130 of the cable arranger 120 is actuated by the controller 128, causing the cable arranger 120 to act on the cable by imparting another rotary motion to the catheter 122 that counteracts the twisting force or displaces the twist away from the operator.

In the embodiment of FIG. 9, the sensor 124 is a magnetic field sensor having three mutually orthogonal coils 132. In the presence of magnetic fields generated by one or more magnetic field generators 134. This arrangement has been implemented for location tracking in the above-described CARTO system, and is capable of detecting changes in orientation, position, and rotation of the catheter 122.

In another embodiment, the sensor 124 may be replaced by an array of three mutually orthogonal accelerometers mounted at fixed radial distances from the longitudinal axis of the catheter 122. The angular velocity of the catheter 122 and its angular displacement from a nominal position can be derived from the tangential accelerations measured by the accelerometers.

Figure 10:
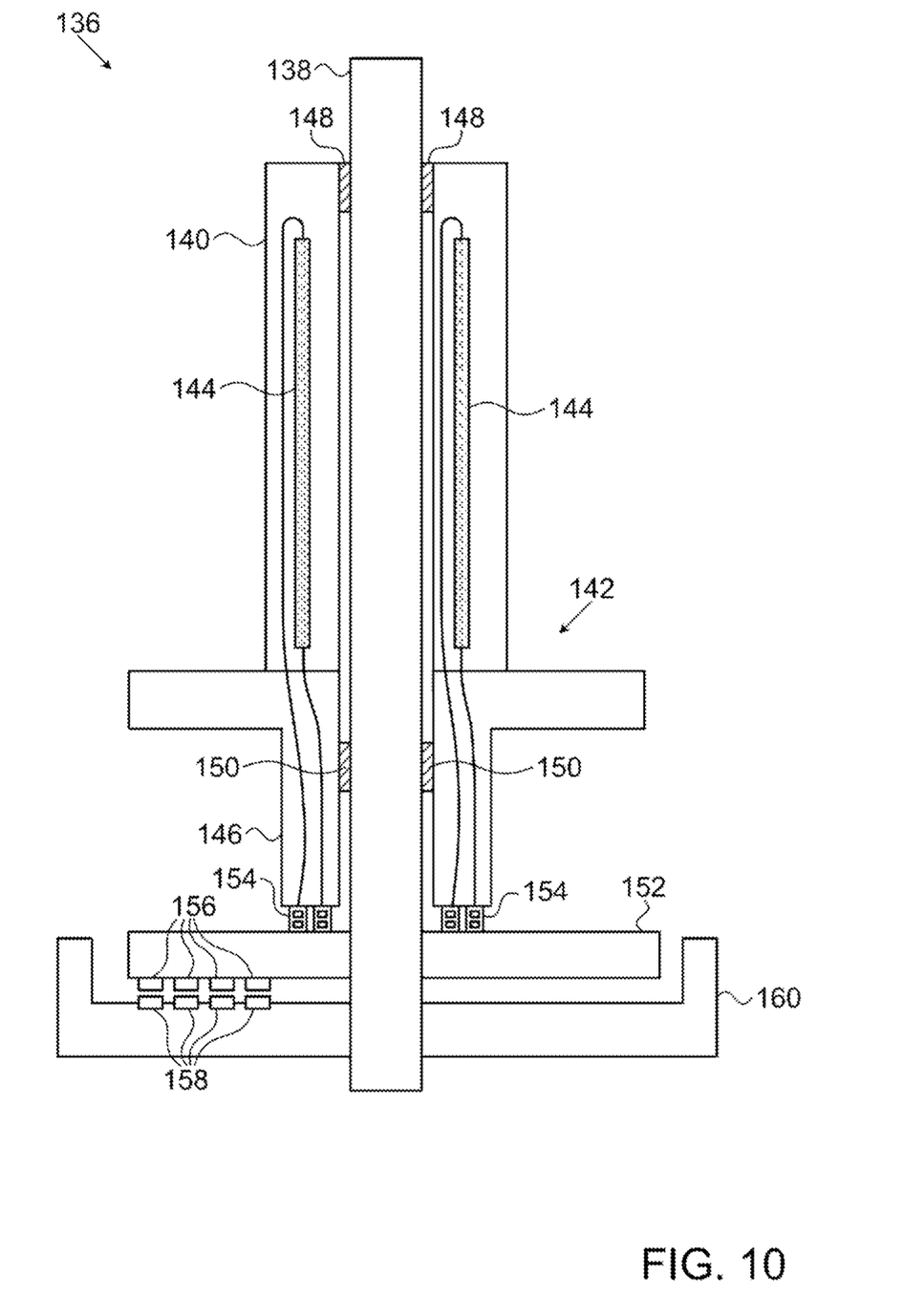
FIG. 10 is a schematic cross sectional view of a rotary torque transducer in accordance with an alternate embodiment of the invention.

In yet another embodiment, the sensor 124 may be replaced by a strain gauge, wherein the torsion rod 54 (FIG. 5) is embodied as a rotary torque transducer applied to the cable. Reference is now made to FIG. 10, which is a schematic cross sectional of a view of a rotary torque transducer 136 in accordance with an alternate embodiment of the invention. A cable 138 passing through the torque transducer 136 is held against a resilient upper segment 140 of a torsion rod 142. Two preloaded strain gauges 144 are incorporated in the upper segment 140, enabling measurement of rotational torque in positive and negative directions.

A lower segment 146 The cable 138 is gripped against the upper segment 140 and lower segment 146 by clasps 148, 150, respectively. The strain gauges 144 are in electrical contact with a slotted gear 152 via fixed electrical contacts 154. The opposite face of the gear 152 has a series of moving electrical contacts 156 of stationary electrical brushes 158 that are mounted on a base 160.

In yet another embodiment, the sensor 124 may be replaced by incorporating a torque encoder in the cable arranger 40 (FIG. 1). A suitable torque encoder is taught in commonly assigned, copending application Ser. No. 14/139,974, filed Dec. 24, 2013, which is herein incorporated by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:
    a catheter adapted for insertion into a living subject, the catheter having a longitudinal axis;
    a cable having one end attached to the catheter and another end at a fixed point of attachment;
    a sensor for detecting a twisting motion of the catheter about the longitudinal axis in a first rotary direction, the twisting motion causing a segment of the cable to form a twist in a portion of the cable;
    a cable arranger comprising a housing and a drive assembly operative for rotating the cable in a second rotary direction that tends to counteract the twisting motion in the first rotary direction for removing the twist from the portion of the cable;
    a controller receiving signals from the sensor and operative for generating control signals to actuate the drive assembly responsively to the signals of the sensor; and
    a torsion rod that extends out from the cable arranger, the torsion rod arranged to grip the cable;
    wherein the housing comprises a first radial slot;
    wherein the drive assembly comprises a drive gear with a second radial slot; and wherein the first radial slot is alignable with the second radial slot to enable ingress and egress of the cable therethrough.

2. The apparatus according to claim 1, wherein the sensor is a magnetic field sensor.

3. The apparatus according to claim 1, wherein the sensor is an accelerometer adapted to measure tangential acceleration of the catheter about the longitudinal axis.

4. The apparatus according to claim 1, wherein the sensor is a rotary torque transducer.

5. The apparatus according to claim 1, wherein the drive assembly of the cable arranger comprises:
    a shaft holding the segment of the cable; and
    a drive motor for rotating the shaft.

6. The apparatus according to claim 5, wherein the shaft has a lumen, the cable passing through the lumen and being in contact with the shaft for rotation therewith.

7. The apparatus according to claim 6, further comprising a gear train linked to the drive motor and the shaft.

8. The apparatus according to claim 7, wherein the gear train comprises the drive gear attached to the drive motor, two linking gears meshing with the drive gear, and a shaft gear meshing with the two linking gears, the shaft gear being concentric with the shaft.

9. The apparatus according to claim 1, wherein the cable comprises a bundle of electrical and hydraulic channels.

10. The apparatus of claim 1, wherein the torsion rod comprises a plurality of portions joined together at a seam, the plurality of portions are capable of being snapped together to grip the cable.

* * * * *